United States Patent [19]
Walker

[11] Patent Number: 5,702,380
[45] Date of Patent: Dec. 30, 1997

[54] SANITARY NAPKIN

[76] Inventor: Rosemary Walker, 112 E. North St., Clayton, N.J. 08312

[21] Appl. No.: 606,064

[22] Filed: Feb. 23, 1996

[51] Int. Cl.$^6$ .................................................. A61F 13/15
[52] U.S. Cl. ........................ 604/385.1; 604/378; 604/387
[58] Field of Search .............................. 604/289, 378, 604/383, 385.1, 387

[56] References Cited

U.S. PATENT DOCUMENTS

| | | | |
|---|---|---|---|
| D. 336,549 | 6/1993 | Stabile | D29/20 |
| D. 352,351 | 11/1994 | Garth | D24/125 |
| 2,852,026 | 9/1958 | Karowski (Karr) | 128/290 |
| 3,896,807 | 7/1975 | Buchalter | 604/289 |
| 4,781,713 | 11/1988 | Welch et al. | 604/385.1 |
| 4,828,555 | 5/1989 | Hermansson | 606/379 |
| 5,241,710 | 9/1993 | Lockhart | 2/406 |
| 5,261,900 | 11/1993 | Houle et al. | 604/385.1 |
| 5,336,208 | 8/1994 | Rosenbluth et al. | 604/329 |
| 5,383,868 | 1/1995 | Hyun | 604/385.1 |
| 5,484,429 | 1/1996 | Vukos et al. | 604/378 |

*Primary Examiner*—Robert A. Clarke
*Attorney, Agent, or Firm*—Lennox & Murtha, P.A.

[57] ABSTRACT

A sanitary napkin that includes an elongate liquid-absorbent main pad body shaped to fit between a woman's thighs, an upper cover to promote flow to the body, a bottom cover to prevent flow out the bottom of the body, a vertical raised elongate pad section extending upwardly to an upper convex arcuate edge to extend between the labia of a woman but not into the woman's vagina, and wicking material extending from the raised elongate pad section to the main pad body to promote flow from the raised section to the main pad body.

2 Claims, 2 Drawing Sheets

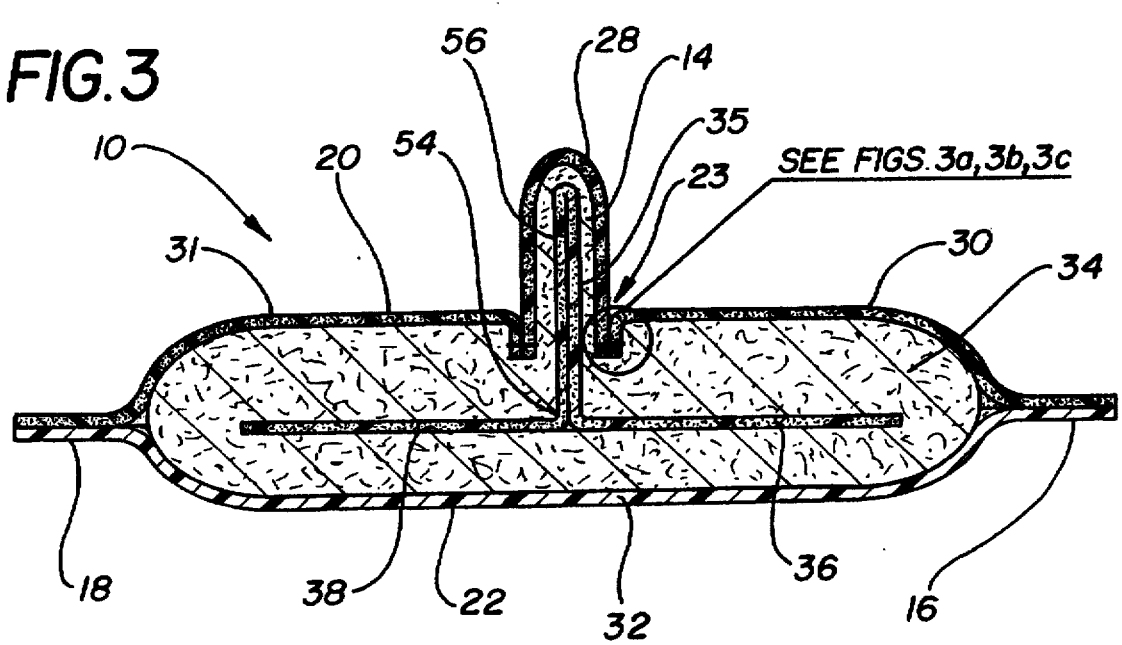
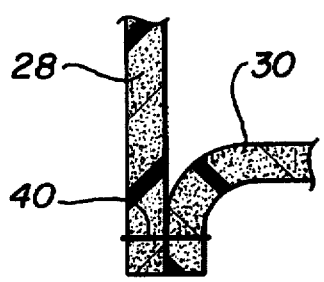
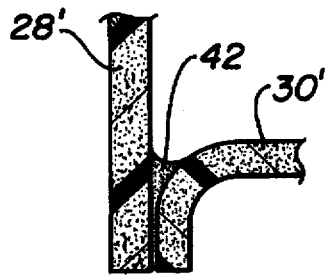
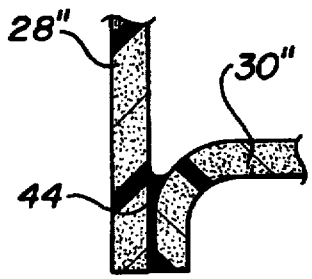
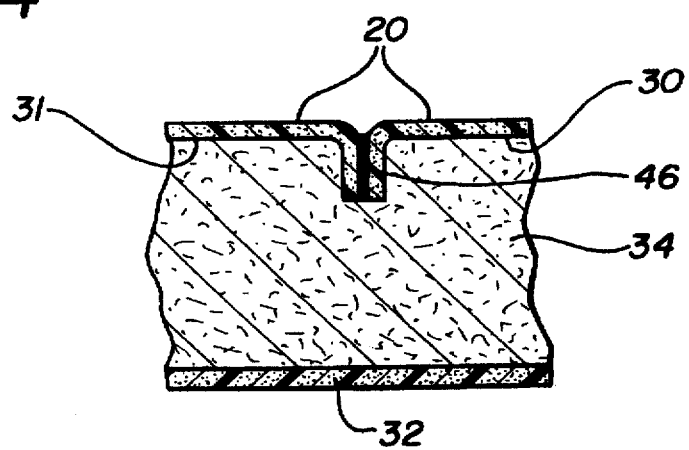

SANITARY NAPKIN

BACKGROUND OF THE INVENTION

This invention involves a sanitary napkin with improved capability of collecting menstrual flow.

While there are a number of sanitary pad improvements and forms, the present external sanitary pad is merely a absorbent catch basin to receive the menstrual flow from the woman's vagina. The alternative construction is the TAMPAX® absorbing device, although many women prefer the external pad construction.

A major problem of the external pad is effective capacity in times of highest menstrual flow. Despite attempted improvements, the pad, by its very nature, becomes saturated and even overflowing in the center leaving the ends of the pad essentially dry. Thus, although the pads are large enough and have sufficient absorbency capabilities to contain normal flows, many women still experience overflows using the standard pad construction.

A number of prior art devices have been constructed including U.S. Pat. Nos. Des. 350,200 and Des. 352,351 illustrating typical external pad designs. A sanitary napkin encased in impermeable film includes an attached porous absorbent plug that is inserted into the woman's vagina thus combining the external and insertable types is described in U.S. Pat. No. 5,383,868 to Hyun. A diaper with padded raised side sections and a raised center section is shown in U.S. Pat. No. 4,828,555 to Hermansson. An incontinence pad with an elongated cup with an ovoid shaped rim to fit against the woman's vulva is described in U.S. Pat. No. 4,781,713 Welch et al. In U.S. Pat. No. 2,852,026 to Karr, a sanitary pad is formed by folding over a center section to form a raised higher absorbing center section. A two piece sanitary panty is described in U.S. Pat. No. 5,241,710 to Lockhart, where the crotch section with a raised absorbent pad is removable. In U.S. Pat. No. 5,336,208 to Rosenblurb a urinary incontinence pad with edges shaped to be inserted under the labia minora with a raised center section extending outwardly.

None of these devices entirely satisfy the needs described above nor attain the objects of this invention provided herein below.

SUMMARY OF INVENTION

It is an object of the protection sought to provide an improved sanitary pad that more effectively transfers the menstrual flow throughout the entire body of the sanitary pad increasing the effective capacity of the pad.

It is a further object of the protection sought to provide a sanitary pad that avoids the discomfort of the menstrual fluid flowing out over the woman's labia to drop onto the standard shaped flat sanitary pad.

It is a particular object of the protection sought to provide a sanitary pad that will fit against the vaginal opening between the labia to collect the menstrual flow. The pad is specifically not constructed to be inserted into the vagina thus avoiding any attendant problems of the insertable type menstrual collecting devices.

It is an additional object of the protection sought to provide a pad that will provide comfort against the vaginal opening employing non-adhering surface materials which effectively wick the fluids into the absorbent packing in the pad.

An aspect of the invention is a sanitary napkin device that includes an elongate liquid-absorbent main pad body that includes a longitudinal axis, a transverse axis with a transverse width adapted for placement between a woman's thighs without folding, a top surface, and a bottom surface. The device further includes first cover means covering the top surface of the main pad body to promote transfer of liquid coming into contact with said means to the main pad body and second cover means on bottom surface of the main pad body to prevent transfer of liquid out the bottom surface of the main pad body. The device further includes a raised elongate pad section attached to the main pad body and aligned along the longitudinal axis of the main pad body, said pad section. The raise elongate pad section includes an upper convex arcuate edge, and a height above the top surface of the main pad body sufficiently high to extend between the labia of a woman, when said top surface is held against the labia, but sufficiently low so as not to extend into the woman's vagina. The sanitary pad device further includes wicking means extending from the raised elongate pad section to the main pad body to promote liquid flow from the raised elongate pad section to the main pad body.

It is preferred that the wicking means extend from a centrally located area of the raised elongate pad section into a centrally located area of the main pad body. It is further preferred that the upper surface of the main pad body and an outer surface of the raised elongate pad section be treated with a hydrophobic oil. It is further preferred that the wicking means include a sheet body having a vertical lateral cross-sectional shape of an inverted "T", an elongate vertical section of the sheet body extending upwardly centrally into the raised elongate pad section from a proximately centrally located line extending longitudinally within the main pad body, and an elongate horizontal section of the sheet body extending laterally outwardly from a lower end of said vertical section proximately centrally located within the main pad body.

BRIEF DESCRIPTION OF THE DRAWINGS

FIG. 3 is a cross-sectional view taken along lines 3—3 on FIG. 1.

FIG. 3a is an enlarged cross-sectional view of a seam in FIG. 3.

FIG. 3b is an enlarged cross-sectional view of an alternative seam for FIG. 3.

FIG. 3c is an enlarged cross-sectional view of a second alternative seam for FIG. 3.

FIG. 4 is a cross-sectional view taken along lines 4—4 on FIG. 1.

DESCRIPTION OF PREFERRED EMBODIMENTS

Figure 1:
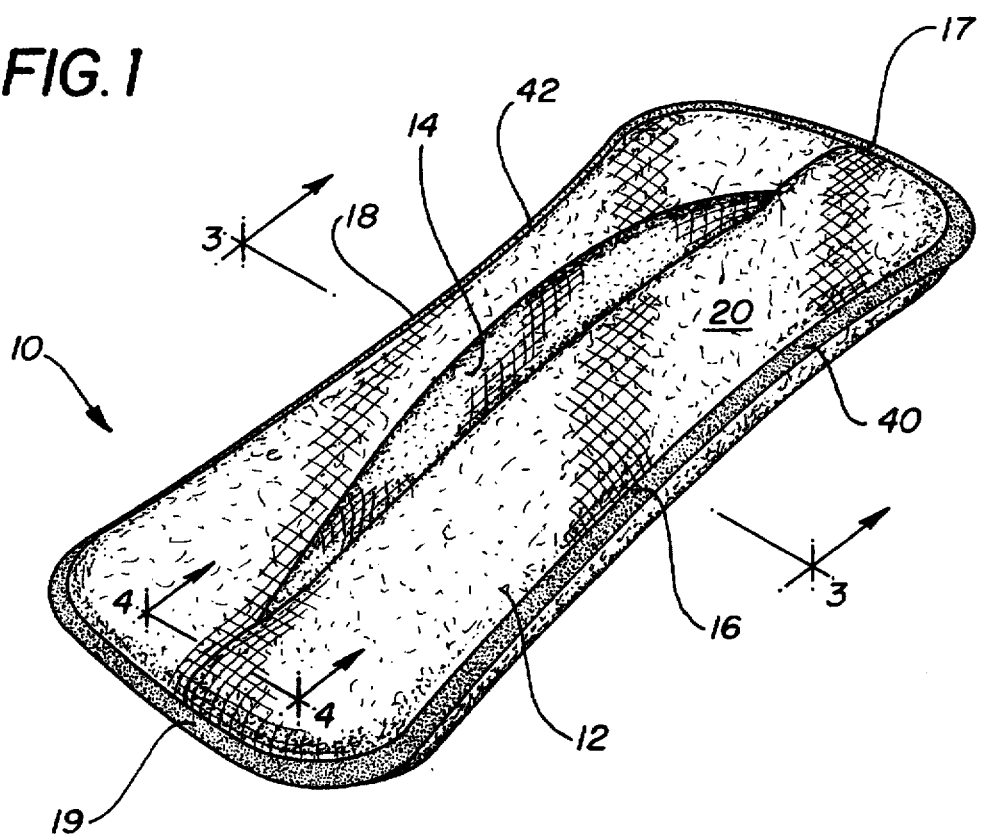
FIG. 1 is a top frontal right side perspective view of sanitary pad of the present invention.
Figure 2:
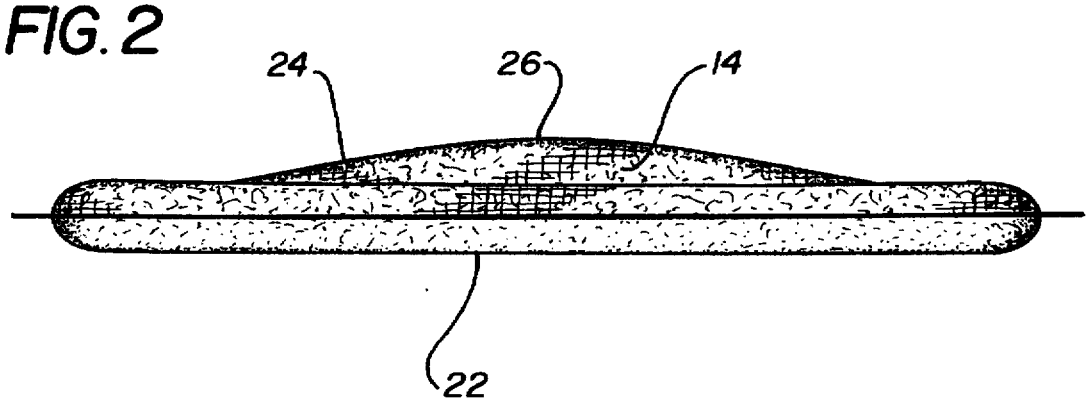
FIG. 2 is a right side elevational view thereof.

Sanitary napkin 10 is illustrated in FIGS. 1 and 2 and the subsequent cross-sectional views. Sanitary napkin 10 includes two main parts, liquid-absorbent pad body 12 and raised elongated pad section 14. Pad body 12 has most of top surface 20 covered by right cover sheet section 30 and left cover sheet section 31. Bottom 22 is covered with impervious plastic sheet 32. Right longitudinal edge 16, left longitudinal edge 18, and end edges 17 and 19 are formed by heat sealing the outer edges of sheets 30, 31, and 32 together. Raised elongate center aligned pad section 14 rises out of the longitudinal center line of pad 12 and has upper arcuate upper edge 14 with center convex section 24.

Elongate section 14 is shaped to fit between the woman's labia positioned to receive menstrual flow and carry that liquid to the body of sanitary napkin 12. Section 14 is covered with cover sheet 28 which is chosen as a material to wick and transport the fluids toward pad body 12 while maintaining as dry a surface as possible. A light application of mineral oil to the porous sheet covering aids in the comfort to the wearer. As particularly shown in FIG. 3, wicking of liquid from section 14 to absorbent packing 34 in body 12 is accomplished by wicking device 54, which is a continuous sheet of wicking material formed as an inverted "T" cross section aligned transversely with upper vertical section 56, being a doubled over wicking sheet extending up into section 14 to wick fluids downwardly to horizontal right wing sheet section 58 and horizontal left wing sheet section 60 extending outwardly into absorbing material 34 of the main pad body to wick materials to essentially all ends of the main pad. Fluid flows readily through cover sheets 28, 30, and 31 into internal packing 34 of the main pad body. As shown in FIGS. 3a, 3b, and 3c, cover sheet 28 is connected through seam 23 to right upper cover sheet 30 on the top of pad body 12. In this fashion, menstrual flow is wicked away from section 14 and into packing 34 which has greater absorbency capacity. Packing 34 is the standard fibrous packing material used in commercially available sanitary pads. Cover sheet 28 is a fibrous woven or semi woven hydrophobic sheet capable of wicking liquids to the underlying pad. Wicking device 54 is constructed of similar materials with a less dense weave and less binder to achieve maximum wicking from upper section 56 along the fabric to horizontal sections 36 and 38. Typical materials include woven and semi-woven fibrous polypropylene, GORE-TEX® fibers, including plastic filaments and synthetic fibers and like materials. As shown in FIG. 3a, the expanded view of seam 23 connected together with stitch 40 illustrates an attachment of sheet 28 covering section 14 to cover sheet 30. In FIG. 3b, hot melt adhesive 42 is used to hold seam 23' together. In FIG. 3c heat seal 44 holds seam 23" together. In FIG. 4, seam 46 is heat sealed to join the adjoining edges of sheets 30 and 31 on upper surface in FIGS. 3 and 4, the elements with the designated "'" or "''" elements that are similar, if not identical, to the corresponding element in a prior figure.

While this invention has been described with reference to specific embodiments disclosed herein, it is not confined to the details set forth and the patent is intended to include modifications and changes which may come within and extend from the following claims.

I claim:
1. A sanitary napkin comprising:

(a) an elongate liquid-absorbent main pad body comprising:
  (i) a longitudinal axis,
  (ii) a transverse axis with a transverse width adapted for placement between a woman's thighs without folding,
  (iii) a top surface, and
  (iv) a bottom surface, (b) first cover means covering the top surface of the main pad body to promote transfer of liquid coming into contact with said first cover means means to the main pad body, (c) second cover means on bottom surface of the main pad body to prevent transfer of liquid out the bottom surface of the main pad body, (d) a raised elongate pad section attached to the main pad body and aligned along the longitudinal axis of the main pad body, said pad section comprising:
  (i) an upper convex arcuate edge, and
  (ii) a height above the top surface of the main pad body sufficiently high to extend between the labia of a woman, when said top surface is held against the labia, but sufficiently low so as not to extend into the woman's vagina, and (e) wicking means extending from the raised elongate pad section to the main pad body to promote liquid flow from the raised elongate pad section to the main pad body comprising:
  (i) a sheet body having a vertical lateral cross-sectional shape of an inverted "T",
  (ii) an elongate vertical section of the sheet body extending upwardly centrally into the raised elongate pad section from a proximately centrally located line extending longitudinally within the main pad body, and
  (iii) an elongate horizontal section of the sheet body extending laterally outwardly from a lower end of said vertical section proximately centrally located within the main pad body.

2. The sanitary napkin of claim 1 wherein the upper surface of the main pad body and an outer surface of the raised elongate pad section is treated with a hydrophobic oil.

* * * * *